United States Patent
Nishio et al.

(10) Patent No.: US 10,038,299 B2
(45) Date of Patent: Jul. 31, 2018

(54) LIGHT SOURCE DEVICE AND HEAT PROCESSING DEVICE FOR LIGHT SOURCE

(71) Applicant: OLYMPUS CORPORATION, Tokyo (JP)

(72) Inventors: Masahiro Nishio, Hachioji (JP); Takeshi Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/990,953

(22) Filed: Jan. 8, 2016

(65) Prior Publication Data
US 2016/0126698 A1 May 5, 2016

Related U.S. Application Data

(63) Continuation of application No. PCT/JP2014/067410, filed on Jun. 30, 2014.

(30) Foreign Application Priority Data

Jul. 9, 2013 (JP) .................................. 2013-143858

(51) Int. Cl.
*H01S 3/04* (2006.01)
*H01S 5/00* (2006.01)
(Continued)

(52) U.S. Cl.
CPC ........ *H01S 5/02469* (2013.01); *A61B 1/0661* (2013.01); *A61B 1/128* (2013.01);
(Continued)

(58) Field of Classification Search
CPC ............. H01S 5/02469; H01S 3/06704; H01S 5/06804; H01S 5/0612; H01S 5/0014; H01S 5/4087; A61B 1/0661; A61B 1/128
See application file for complete search history.

(56) References Cited

U.S. PATENT DOCUMENTS 7,248,614 B2 * 7/2007 Yamazaki .......... B23K 26/0604
 372/64
8,251,897 B2 8/2012 Mizuyoshi
(Continued)

FOREIGN PATENT DOCUMENTS

CN 101131232 A1 2/2008
JP 2002-095624 A 4/2002
(Continued)

OTHER PUBLICATIONS

English Translation of JP2002-95624.*
(Continued)

*Primary Examiner* — Yuanda Zhang
(74) *Attorney, Agent, or Firm* — Scully, Scott, Murphy & Presser, P.C.

(57) ABSTRACT

A light source device includes a plurality of light source units, a plurality of first heat processing units, a second heat processing unit, a plurality of thermal connectors, a light processing unit, and a plurality of optical connectors. The plurality of thermal connectors make the plurality of first heat processing units and the second heat processing unit attachable to and detachable from each other, and thermally connect the plurality of first heat processing units and the second heat processing unit. The light processing unit processes the light output from the plurality of light source units. The plurality of optical connectors make the plurality of light source units and the light processing unit attachable to and detachable from each other, and optically connect the plurality of light source units and the light processing unit.

16 Claims, 10 Drawing Sheets

(51) Int. Cl.
*H01S 5/024* (2006.01)
*H01S 5/068* (2006.01)
*H01S 5/06* (2006.01)
*H01S 3/067* (2006.01)
*A61B 1/06* (2006.01)
*A61B 1/12* (2006.01)
*H01S 5/40* (2006.01)

(52) U.S. Cl.
CPC ........ *H01S 3/06704* (2013.01); *H01S 5/0014* (2013.01); *H01S 5/0612* (2013.01); *H01S 5/06804* (2013.01); *H01S 5/4087* (2013.01)

(56) References Cited

U.S. PATENT DOCUMENTS

| | | | |
|---|---|---|---|
| 8,564,651 | B2 | 10/2013 | Ozawa et al. |
| 8,724,668 | B2 * | 5/2014 | Yabe .................... G02B 6/4201 362/235 |
| 2003/0142712 | A1 | 7/2003 | Ikeda et al. |
| 2012/0287954 | A1 | 11/2012 | Saruwatari et al. |

FOREIGN PATENT DOCUMENTS

| | | |
|---|---|---|
| JP | 2004-259824 A | 9/2004 |
| JP | 2006-043272 A | 2/2006 |
| JP | 2006-269182 A | 10/2006 |
| JP | 2007-59930 A | 3/2007 |
| JP | 2009-189463 A | 8/2009 |
| JP | 2011-067268 A | 4/2011 |
| JP | 2012-217483 A | 11/2012 |
| JP | 2013-34546 A | 2/2013 |

OTHER PUBLICATIONS

English Translation of JP2013-34546.*
Chinese Office Action dated Oct. 8, 2016 in related Chinese Patent Application No. 201480034235.0.
Extended Supplementary European Search Report dated Feb. 2, 2017 in related European Patent Application No. 14 82 3589.8.
English translation of International Preliminary Report on Patentability dated Jan. 21, 2016 together with the Written Opinion received in related International Application No. PCT/JP2014/067410.
International Search Report dated Sep. 22, 2014 issued in PCT/JP2014/067410.
Japanese Office Action dated Jun. 6, 2017 received in Japanese Patent Application No. 2013-143858, together with an English-language translation.
Chinese Office Action dated Jun. 15, 2017 received in Chinese Application No. 201480034235.0, together with an English-language translation.
Japanese Office Action dated Jan. 16, 2018 received in Japanese Patent Application No. 2013-143858, together with an English-language translation.

* cited by examiner

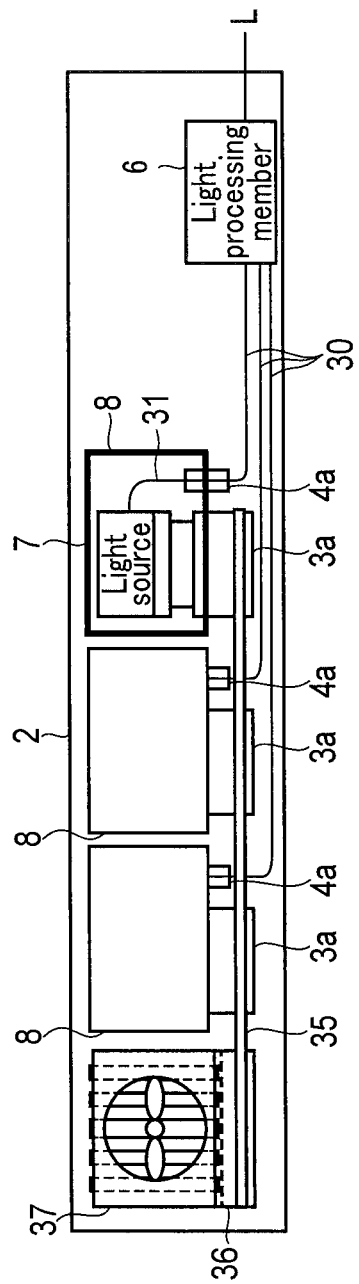

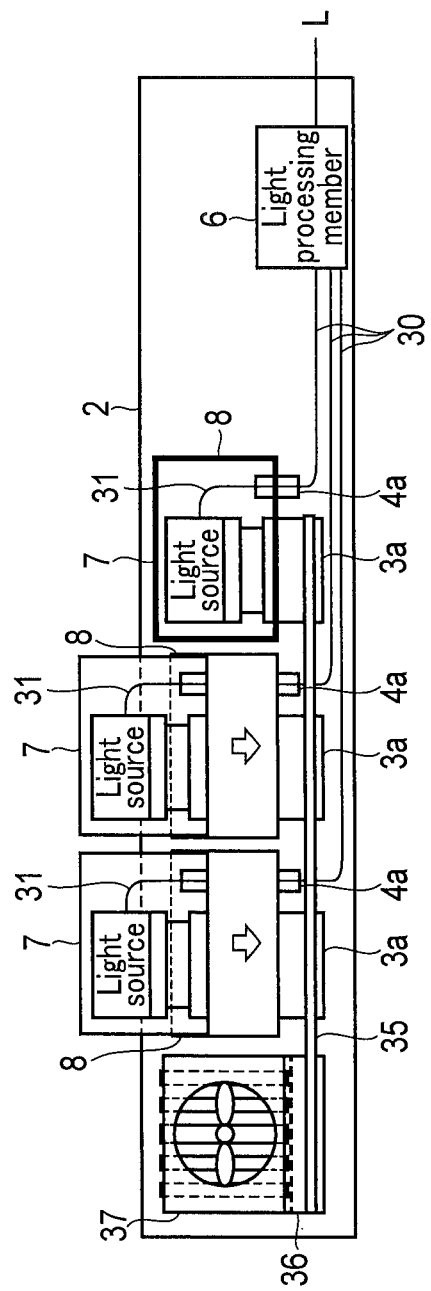
F I G. 3B

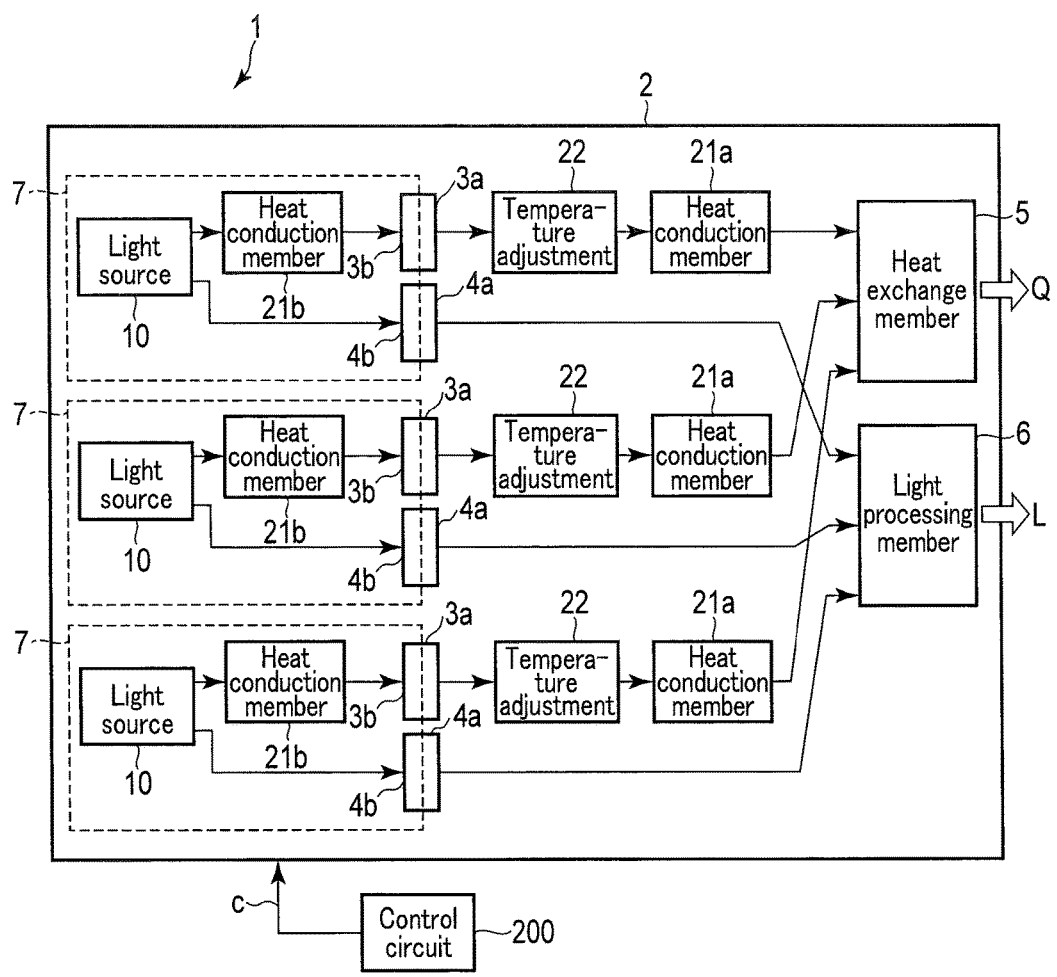
F I G. 9A

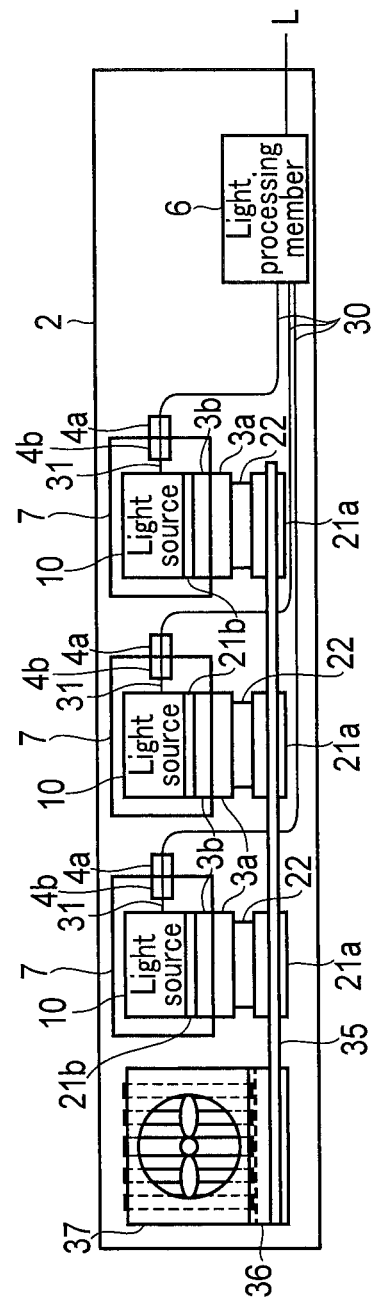
F I G. 10

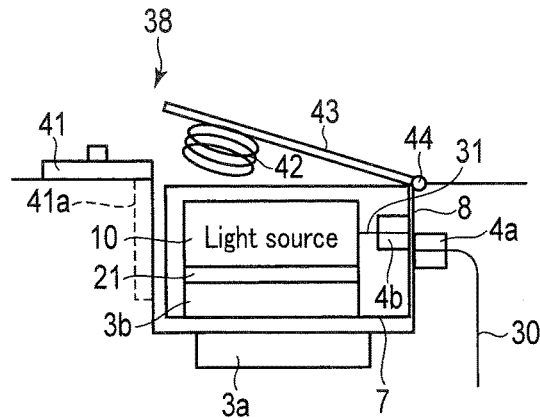
F I G. 11A
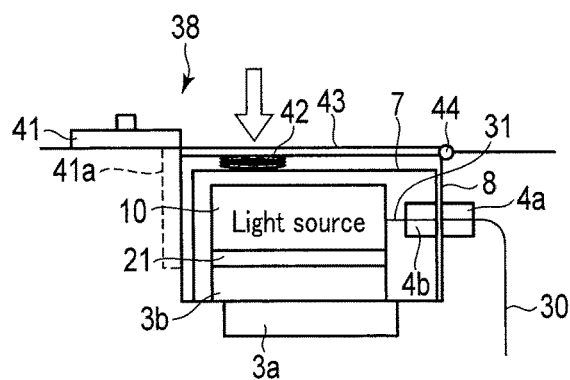
F I G. 11B
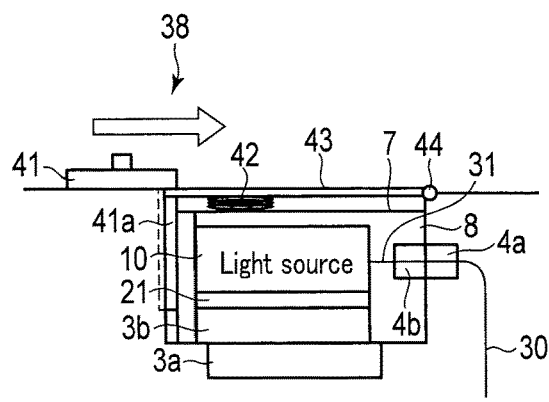
F I G. 11C

LIGHT SOURCE DEVICE AND HEAT PROCESSING DEVICE FOR LIGHT SOURCE

CROSS-REFERENCE TO RELATED APPLICATIONS

This application is a Continuation Application of PCT Application No. PCT/JP2014/067410, filed Jun. 30, 2014 and based upon and claiming the benefit of priority from the prior Japanese Patent Application No. 2013-143858, filed Jul. 9, 2013, the entire contents of which are incorporated herein by reference.

BACKGROUND OF THE INVENTION

1. Field of the Invention

The present invention relates to a light source device and a heat processing device for light source.

2. Description of the Related Art

As a light source device, for example, a device is known in which light is emitted from a laser light source and an object is irradiated with the light through an optical fiber. The light source generates heat and thus needs to be cooled for its stable operation.

Jpn. Pat. Appln. KOKAI Publication No. 2004-259824 (PTL 1) discloses a light source device for efficiently cooling a number of laser diode (LD) light sources with the same wavelength. The light source device of this literature includes a heat sink having a planar base back side from which a plurality of fins rise. On a base front side of the heat sink, a number of LD light sources are arranged in a staggered manner (a staggered arrangement). In this light source device, heat generated from each of the LD light sources is radiated and cooled by applying cooled air to the fins of the heat sink.

BRIEF SUMMARY OF THE INVENTION

According to an aspect of the present invention, there is provided a light source device including: a housing; a plurality of light source units which are attachable to and detachable from the housing and which output light; a plurality of first heat processing units which are respectively provided in the plurality of light source units and which process heat generated from the plurality of light source units; a second heat processing unit which is provided in the housing and which processes heat conducted from each of the plurality of first heat processing units; a plurality of thermal connectors which make the plurality of first heat processing units and the second heat processing unit attachable to and detachable from each other and which thermally connect the plurality of first heat processing units and the second heat processing unit; a light processing unit which is provided in the housing and which processes the light output from the plurality of light source units; and a plurality of optical connectors which make the plurality of light source units and the light processing unit attachable to and detachable from each other and which optically connect the plurality of light source units and the light processing unit.

According to another aspect of the present invention, there is provided a heat processing device for light source including: a housing; a plurality of placement units which attaches each of a plurality of light sources in the housing; a heat processing unit which processes heat; and a plurality of thermal connectors which make the plurality of light sources and the heat processing unit attachable to and detachable from each other, thermally connect the plurality of light sources and the heat processing unit, and conducts heat generated from the light source placed in each of the placement units to the heat processing unit.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3A is a schematic configuration diagram showing attachment of a light source module in the device.

FIG. 3B is a schematic configuration diagram showing attachment of the light source module in the device.

FIG. 9A is a block diagram showing a light source device of a second embodiment of the present invention.

FIG. 10 is a schematic diagram showing attachment of a light source module of the device.

FIG. 11A is a schematic diagram showing a pressure mechanism of a modification to the embodiment.

FIG. 11B is a schematic diagram showing the pressure mechanism of the modification to the embodiment.

FIG. 11C is a schematic diagram showing the pressure mechanism of the modification to the embodiment.

DETAILED DESCRIPTION OF THE INVENTION

First Embodiment

A first embodiment will be described below with reference to the drawings.

Figure 1A:
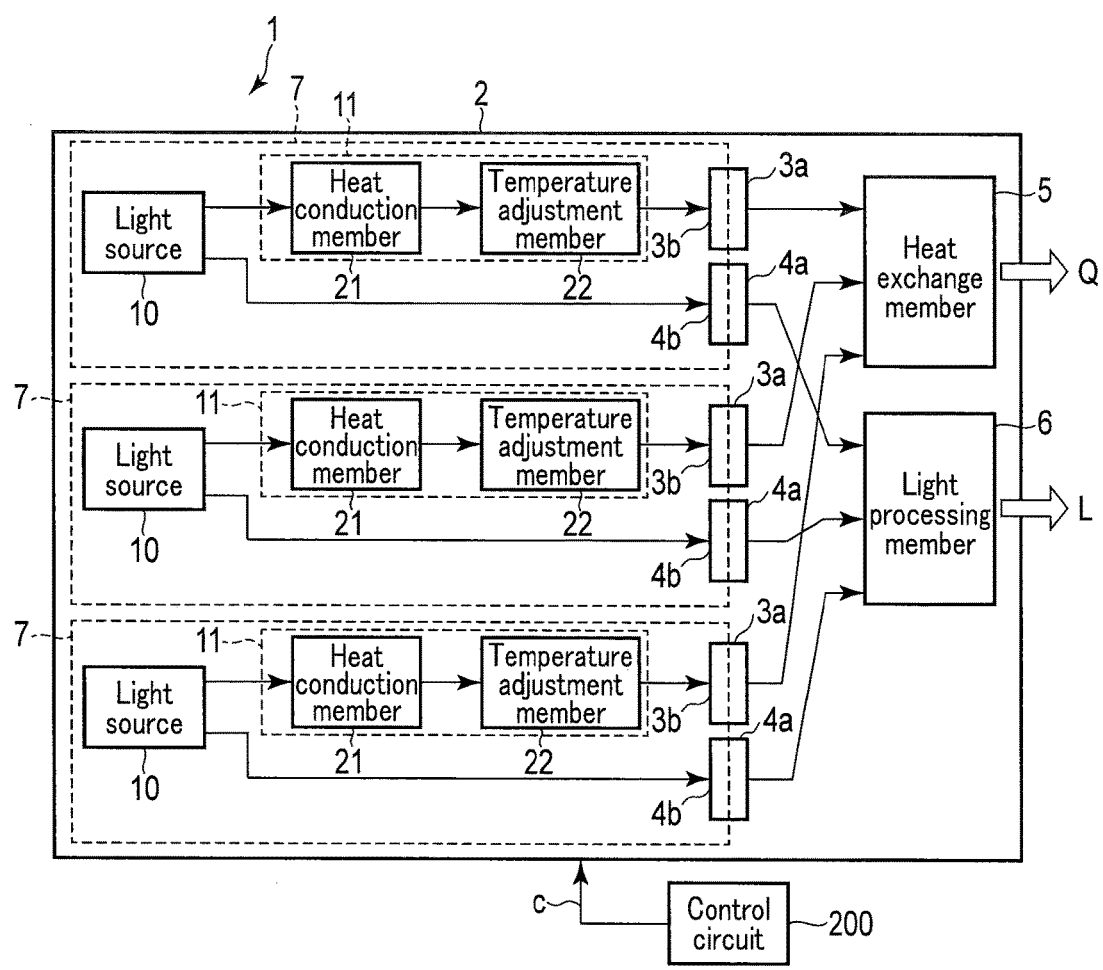
FIG. 1A is a block diagram showing a light source device of a first embodiment of the present invention.
Figure 1B:
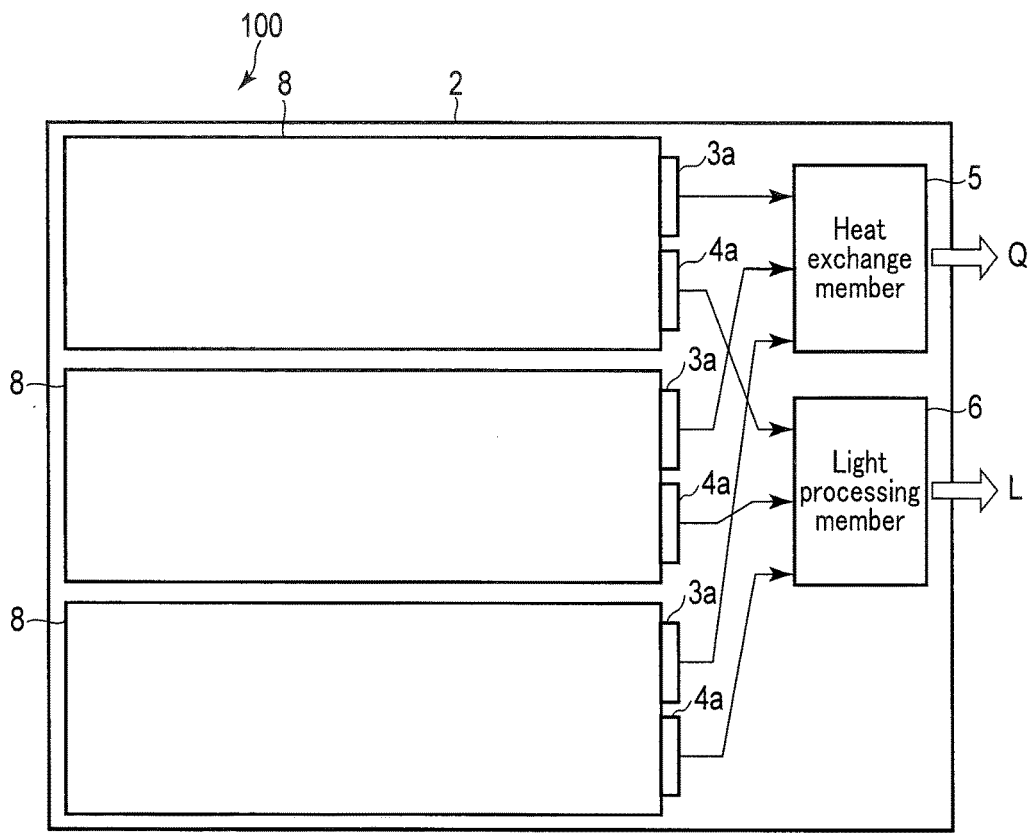
FIG. 1B is a block diagram showing a heat processing device for light source of the embodiment.
Figure 2:
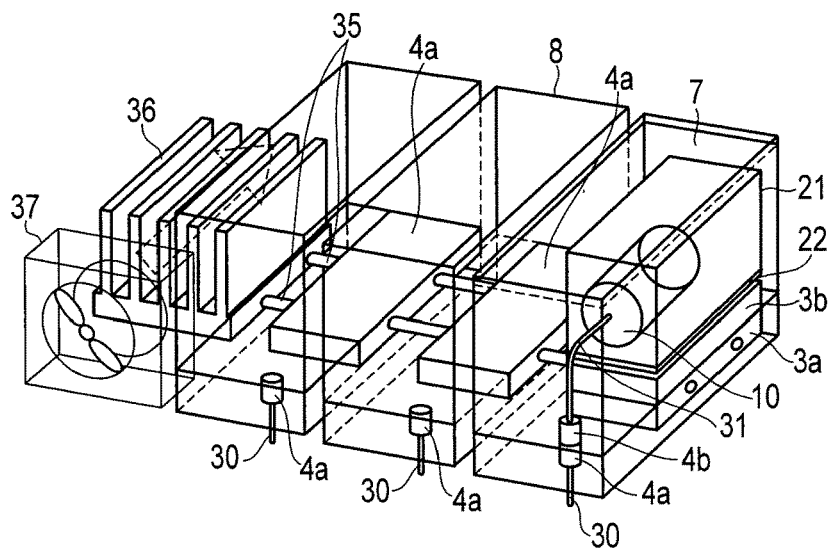
FIG. 2 is a schematic perspective view of the light source device of the embodiment.

FIG. 1A is a block diagram of a light source device 1. FIG. 1B is a block diagram of a heat processing device for light source 100. FIG. 2 is a perspective view of the light source device 1. FIG. 3A is a schematic configuration diagram showing attachment of a light source module 7. FIG. 3B is a schematic diagram of attachment of the light source module 7.

In the light source device 1, as shown in FIG. 1A, at least one light source module 7 is placed. A heat processing device for light source 100 including a light source module 7 is referred to as a light source device 1. Conversely, as shown in FIG. 1B, a light source device 1 including no light source modules 7 is referred to as a heat processing device for light source 100.

The light source device 1 (heat processing device for light source 100) includes a housing 2. In the housing 2, a plurality of second thermal connectors 3a, a plurality of second optical connectors 4a, a heat exchange member 5, a light processing member 6 and a plurality of slots 8 are arranged. As shown in FIG. 1A, for example, three second thermal connectors 3a, three second optical connectors 4a and three slots 8 are arranged, but the number is not limited to three. The number of second thermal connectors 3a, that of second optical connectors 4a and that of slots 8 each can be varied according to an object to be observed and a method of observation.

As shown in FIG. 2, each of the light source modules 7 is placed in the housing 2 by attaching it to one of a plurality of slots (placement sections) 8 formed in the housing 2. One light source module 7 can be attached to and detached from each of the slots 8. As shown in FIGS. 3A and 3B, each of the light source modules 7 is inserted into the slot 8 from the top and attached thereto. Each of the light source modules 7 is easily attached to and detached from any one of the slots 8.

Specifically, in the heat processing device for light source 100, three slots 8 are provided in the housing 2 as shown in FIGS. 1B to 3B. The three slots 8 are arranged in the same direction, such as the longitudinal direction of the housing 2. As described above, the light source modules 7 can be attached to and detached from the respective slots 8. When the three light source modules 7 are attached to their respective slots 8, they are arranged in parallel to one another. These light source modules 7 are thus arranged in the longitudinal direction of the heat processing device for light source 100.

The second thermal connectors 3a and second optical connectors 4a are each attached to the underside of its corresponding slot 8 in the housing 2. In other words, the second thermal connectors 3a are provided in the housing 2.

Each of the light source modules 7 includes a first thermal connector 3b and a first optical connector 4b. One first thermal connector 3b and one first optical connector 4b are attached to the light source module 7 such that the connectors 3b and 4b may be located at an underside of the slot 8 when the light source module 7 is attached to the slot 8. More specifically, when the light source module 7 is attached to the slot 8, the second thermal connector 3a and the first thermal connector 3b are arranged in such a positional relation that they are thermally connected to each other at the underside of the slot 8. The second thermal connector 3a and first thermal connector 3b can be connected to and detached from each other.

The second thermal connectors 3a are each thermally connected to the heat exchange member 5, as shown in FIG. 1. The heat exchange member 5 collects heat from the respective second thermal connectors 3a and radiates the collected heat Q to the outside.

Each of the first optical connectors 4b and its corresponding one of the second optical connectors 4a are optically connected to each other by surface contact, as shown in FIG. 2. The first optical connectors 4b and the second optical connectors 4a can be connected to and detached from each other. The first optical connectors 4b and the second optical connectors 4a are arranged in such a positional relation that they are connected to each other at the underside of the slot 8.

The second optical connectors 4a are each optically connected to the light processing member 6, as shown in FIG. 1. The light processing member 6 receives light from the respective second light connectors 4a, combines the received light and outputs it as illumination light L. The illumination light L is thus emitted from an end portion of the light source device 1. The light processing member 6 can be designed to output the light in almost the same direction from its close position, without combining the light.

The configuration of the light source modules 7 will specifically be described. Each of the light source modules 7 includes a light source 10, a first heat processing unit 11, the first thermal connector 3b and the optical connector 4b, as shown in FIGS. 1A and 2. The first heat processing unit 11 includes a heat conduction member 21 and a temperature adjustment member 22.

The light source 10 includes one laser diode (LD). For example, the laser diode (LD) of the light source 10 outputs laser light whose wavelength differs from that of the laser diode (LD) of another light source 10. The light source 10 is optically connected to the first optical connector 4b of the light source module 7. The light source 10 and the first optical connector 4b are connected through an optical fiber 31. The light source 10 and the optical fiber 31 are optically coupled through a lens or the like. The light emitted from the light source 10 is collected by the optical fiber 31 through the lens. Thus, the light emitted from the light source 10 is propagated to the first optical connector 4b through the optical fiber 31.

The temperature adjustment member 22 is provided to the light source 10 with the heat conduction member 21 therebetween. For example, the temperature adjustment member 22 is bonded to the heat conduction member 21, as shown in FIG. 2. The temperature adjustment member 22 adjusts the temperature of a surface bonded to the heat conduction member 21 under the control of a control circuit 200, as shown in FIG. 1A. The temperature adjustment member 22 includes, for example, a Peltier device.

The control circuit 200 shown in FIG. 1A controls one temperature adjustment member 22, but it also controls another temperature adjustment member 22. The control circuit 200 is provided inside or outside the housing 2. The control circuit 200 controls drive current of the Peltier device to adjust the temperature of a surface bonded to the heat conduction member 21. Under this control, the temperature adjustment member 22 adjusts the temperature of the light source 10 through the heat conduction member 21. The temperature adjustment member 22 is thermally connected to the first thermal connector 3b and thus the heat conduction member 21 propagates heat to the first thermal connector 3b.

The light source device 1 includes a power supply and the control circuit 200 which are provided inside or outside the housing 2. Though not shown, the light source module 7 includes an electrical connector which allows the light source module 7 to be connected to and detached from the power supply and the control circuit 200, and receives a control signal C from the control circuit 200 through the electrical connector. The control signal C contains information for controlling, for example, power for light emission, timing of light emission and an amount of light emission of the light source 10 as well as a signal for controlling the temperature adjustment members 22.

Figure 4A:
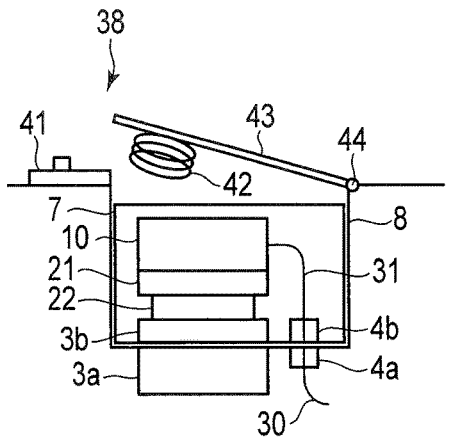
FIG. 4A is a schematic diagram showing a pressure mechanism in the device.
Figure 4B:
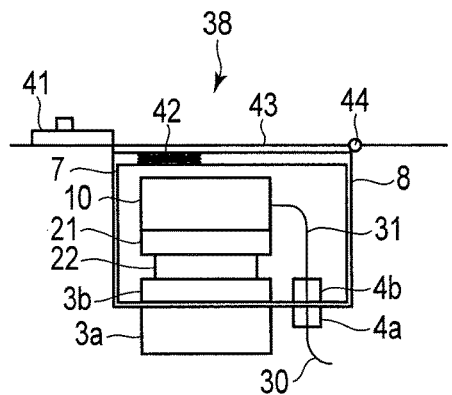
FIG. 4B is a schematic diagram showing the pressure mechanism in the device.

As shown in FIGS. 4A and 4B, a pressure mechanism 38 is provided for the slot 8. The pressure mechanism 38 ensures attachment of the light source module 7. The pressure mechanism 38 includes a cover fixing member 41, a spring section 42, a cover section 43 and a rotation mechanism 44. The cover fixing member 41 is placed slidably to above the slot 8. When the cover fixing member 41 moves to above the slot 8, or to above the cover section 43, it fixes the cover section 43 to prevent the cover section from being opened upwardly. The spring section 42 is provided on the underside of the cover section 43. The underside of the cover section 43 corresponds to the side on which the light source module 7 is placed when the cover section 43 is closed. The spring section 42 applies force downwardly to press the light source module 7. The cover section 43 is so placed that it can be opened and closed above the slot 8. The rotation mechanism 44 is provided above the slot 8. The rotation mechanism 44 is provided with an end portion of the cover section 43. The rotation mechanism 44 supports the cover section 43 rotatably above the slot 8.

With the pressure mechanism 38, the second thermal connector 3a of the housing 2 and the first thermal connector 3b of the light source module 7 are brought into close contact with each other, thus ensuring thermal contact. Optical contact between the optical connector 4a of the housing 2 and the first optical connector 4b of the light source module 7 is ensured.

The housing 2 is provided with heat pipes 35, as shown in FIGS. 2 to 3B. The heat pipes 35 thermally connect the second thermal connector 3a and the heat exchange member 5. When a plurality of second thermal connectors 3a are arranged in series in the housing 2, the heat pipes 35 are placed to penetrate the second thermal connectors 3a. Heat conducted to the second thermal connectors 3a is conducted to the heat exchange member 5 through the heat pipes 35.

The heat pipe 35 is, for example, a pipe into which a volatile liquid is injected. The heat pipe 35 is formed of a high-heat conductive member having high heat conductivity for evaporating and condensing the liquid cyclically. The heat pipe 35 can be formed of a high-heat conductive film such as a graphite sheet. The heat pipes 35 penetrate a flat base of a heat sink 36.

The heat exchange member 5 includes the heat sink 36 and an air-sending fan 37. The heat sink 36 includes, for example, the flat base and a plurality of fins rising upwardly from the base. The fins each extend in a direction orthogonal to the direction of arrangement of the light source modules 7.

The heat conducted to the second thermal connectors 3a is collected in the heat sink 36 of the heat exchange member 5 through the heat pipes 35. The collected heat is radiated from the heat sink 36. The radiated heat is discharged into an atmosphere outside the housing 2.

The air-sending fan 37 sends air in a direction in which the fins extend. Thus, the heat sink 36 increases in its discharge effect.

The heat pipes 35, heat sink 36 and air-sending fan 37 constitute a second heat processing unit.

An operation of the embodiment will be described below.

The light emitted from the light source 10 of each of the light source modules 7 is collected by each lens. The collected light is guided to the first optical connector 4b by the optical fiber 31. The light guided to the first optical connector 4b is incident upon an optical fiber 30 through the second optical connector 4a. The light incident upon the optical fiber 30 is guided to the light processing member 6 by the optical fiber 30.

The light guided to the light processing member 6 from the light source modules 7 is combined by the light processing member 6. The combined light is radiated as illumination light L from the housing 2 to the outside.

In this light source device 1, when one of the light sources 10 emits light, it generates heat. The heat generated from the light source 10 is conducted to the first heat processing unit 11. Specifically, the heat generated from the light source 10 is conducted to the heat conduction member 21. The heat conducted to the heat conduction member 21 is conducted to the first thermal connector 3b through the temperature adjustment member 22.

If the temperature adjustment member 22 is a Peltier device, the temperature adjustment member 22 adjusts the temperature of a surface bonded to the heat conduction member 21 under the control of the control circuit 200. The control circuit 200 adjusts the temperature of a surface bonded to the heat conduction member 21 by controlling the drive current of the Peltier device. Accordingly, the temperature of the light source 10 remains constant. As a result, the light source 10 operates with stable characteristics.

The heat conducted to the first thermal connector 3b is conducted to the second thermal connector 3a. The heat conducted to the second thermal connector 3a is conducted from high temperature to low temperature through the heat pipes 35. In other words, the heat conducted to the second thermal connector 3a is usually conducted to the heat exchange member 5 from the second thermal connector 3a through the heat pipes 35. The heat exchange member 5 radiates the conducted heat from the heat sink 36 and discharges it outside the housing 2 by air sent from the air-sending fan 37.

According to the light source device 1 of the first embodiment so described, a plurality of light source modules 7 are attachably and detachably provided. Specifically, in the light source device 1, the housing 2 includes a plurality of slots 8, and the light source modules 7 are attachably and detachably provided in their respective slots 8. Accordingly, one light source module 7 included in the heat processing device for light source 100 is replaced with another light source module 7 that outputs light with another wavelength to make it possible to change a combination of the wavelengths of light emitted from the light source device 1. As a result, the illumination light L emitted from the light source device 1 can be changed to have a desired wavelength.

The heat generated from the light source 10 is processed by the first heat processing unit 11. The heat processed by the first heat processing unit 11 is conducted to the second heat processing unit (heat pipes 35 and heat exchange member 5 (heat sink 36 and air-sending fan 37)) through the first thermal connector 3b and second thermal connector 3a. The second heat processing unit conducts the conducted heat to the heat exchange member 5 through the heat pipes 35 that are a high-heat conductive member, and discharge it outside the housing 2. Accordingly, the light source 10 is cooled. Since the second heat processing unit is placed in the housing 2 to radiate heat to the outside, the light source module 7 can be downsized.

[First Modification to First Embodiment]

Next, a first modification to the above first embodiment will be described with reference to FIG. 5. For the sake of brevity, the figure shows only a portion of one slot 8. In this modification, the same structural elements as those of the above first embodiment are denoted by the same symbols as those of the first embodiment and their detailed descriptions are omitted.

Figure 5:
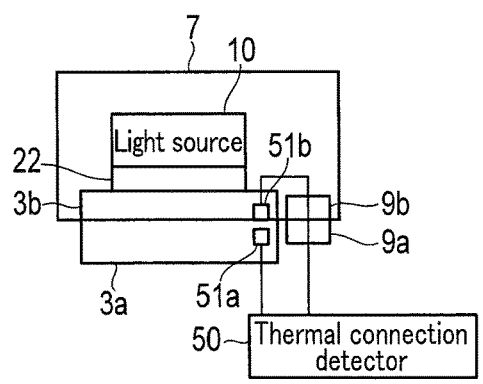
FIG. 5 is a schematic diagram showing a configuration for detecting a thermal connection of a first modification to the embodiment.

FIG. 5 is a configuration diagram of a first modification of the light source device 1. The light source device 1 detects a thermal connection. The light source device 1 differs from that of the first embodiment in part of the structure of a connection between the light source module 7 and the slot 8 in the housing 2.

The light source device 1 includes a structure that allows a thermal connection between the second thermal connector 3a and the first thermal connector 3b to be sensed. Each of the light source modules 7 includes an electrical connector 9b and first thermal connector 3b. The first thermal connector 3b includes a temperature sensor 51b. The temperature sensor 51b senses temperature of the first thermal connector 3b. In other words, the first thermal connector 3b has a portion of low-heat resistance. The temperature sensor 51b is disposed in the portion of low-heat resistance of the first thermal connector 3b. The electrical connector 9b is electrically connected to the temperature sensor 51b through electrical wiring.

The heat processing device for light source 100 includes a plurality of second thermal connectors 3a. The second thermal connectors 3a each include a temperature sensor 51a. The temperature sensor 51a senses temperature of the second thermal connector 3a. The second thermal connector 3a has a portion of low-heat resistance. The temperature sensor 51a is disposed in the portion of low-heat resistance of the second thermal connector 3a.

Each of the slots 8 in the housing 2 includes an electrical connector 9a and a thermal connection detector 50. The thermal connection detector 50 is connected to the electrical connector 9a and the temperature sensor 51a through, e.g., electrical wiring. When the light source module 7 is attached to the slot 8, the electrical connector 9a and the electrical connector 9b are arranged in such a positional relation that they are connected to each other on the underside of the flat slot 8.

The electrical connector 9a and the electrical connector 9b are each a common electrical connector, for example. The light source 10 and the temperature adjustment member (e.g., Peltier device) 22 may be connected to the electrical connector 9b through electrical wiring. In this case, the control circuit 200 is also connected to the electrical connector 9a.

When the light source module 7 is attached to the slot 8, the electrical connector 9b and the electrical connector 9a are connected to each other. The temperature sensor 51b is connected to the electrical connector 9b and the electrical connector 9a. Simultaneously, power is applied to the light source 10 and the temperature adjustment member 22 through the electrical connector 9b and the electrical connector 9a.

As described above, the temperature sensor 51a is connected to the thermal connection detector 50. In other words, the electrical connector 9b and the electrical connector 9a are electrical wiring for connecting each of the light source modules 7 to the thermal connection detector 50. The electrical connector 9b and the electrical connector 9a are electrical wiring for simultaneously connecting each of the light source modules 7 to the control circuit 200 to apply power necessary for operating the light source modules 7 at the same time each of the light source modules 7 is attached to the housing 2.

The thermal connection detector 50 detects whether the first thermal connector 3b and the second thermal connector 3a are thermally connected to each other based upon a temperature difference between the temperature sensed by the temperature sensor 51a and the temperature sensed by the temperature sensor 51b.

Next, an operation of the above first modification will be described.

When the light source device 1 is powered up, the temperature adjustment member 22 is energized by the control circuit 200 through electrical wiring. The temperature adjustment member 22 raises the temperature of the first thermal connector 3b. If the second thermal connector 3a and the first thermal connector 3b are thermally connected, heat of the first thermal connector 3b is conducted to the second thermal connector 3a. Thus, the temperatures sensed by the temperature sensor 51a and the temperature sensor 51b become almost the same.

If the second thermal connector 3a and the first thermal connector 3b are not thermally connected to each other, heat is not conducted; thus, there occurs a temperature difference between the temperatures sensed by the temperature sensor 51a and the temperature sensor 51b.

The thermal connection detector 50 detects a thermal connection between the first thermal connector 3b and the second thermal connector 3a according to the temperature difference between the temperatures sensed by the temperature sensor 51a and the temperature sensor 51b. A result of the detection of the thermal connection detector 50 is sent to the control circuit 200.

If the state of a connection between the second thermal connector 3a and the first thermal connector 3b is bad, the light source 10 may malfunction. In this case, the control circuit 200 performs control to stop operating the light source 10. The state in which the light source 10 malfunctions is, for example, a state in which the light source 10 increases in its temperature because the light source 10 does not discharge heat sufficiently.

As described above, according to the first modification, the temperature sensors 51a and 51b are provided to sense a temperature difference between the first thermal connector 3b and the second thermal connector 3a, thereby making it possible to detect a thermal connection between the first thermal connector 3b and the second thermal connector 3a with reliability. As a result, the light source device 1 is able to detect whether a thermal connection is reliably performed.

The heat processing device for light source 100 may include a display unit. For example, if the state of a thermal connection between the second thermal connector 3a and the first thermal connector 3b is bad, the bad state of a thermal connection can be displayed to a user who uses the light source device 1 on the display unit. Consequently, the user can confirm the bad state of a thermal connection on the display unit. For example, it is possible to urge the user to confirm attachment of the light source module 7 to the housing 2 and reattachment thereof.

If the temperature sensors 51a and 51b have only to be thermally connected to the second and first thermal connectors 3a and 3b without being provided in the second and first thermal connectors 3a and 3b, they can be provided in whatever positions.

To detect a temperature difference between the first thermal connector 3b and the second thermal connector 3a with reliability, it is advisable to compare thermal resistance of the second thermal connector 3a and that of the first thermal connector 3b in case a malfunction occurs.

It is advisable to provide the temperature sensors 51a and 51b in positions where thermal resistance between the second thermal connector 3a and the temperature sensor 51a becomes sufficiently low and thermal resistance between the first thermal connector 3b and the temperature sensor 51b becomes sufficiently low.

[Second Modification to First Embodiment]

Next, a second modification to the above first embodiment will be described with reference to FIG. 6. For the sake of brevity, the figure shows only a portion of one slot 8. In this modification, the same structural elements as those of the above first embodiment are denoted by the same symbols as those of the first embodiment and their detailed descriptions are omitted.

Figure 6:
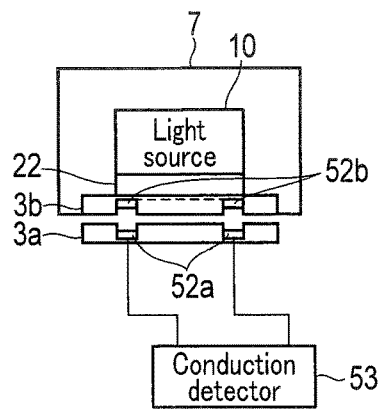
FIG. 6 is a schematic diagram showing a configuration for detecting a thermal connection of a second modification to the embodiment.

FIG. 6 is a schematic configuration diagram of a light source device for detecting a thermal connection according to the second modification to the first embodiment. The light source device 1 differs from that of the first embodiment in part of the structure of a connection between the light source module 7 and the slot 8 in the housing 2.

The light source device 1 according to the second modification senses energization between electrodes to sense a connection between the thermal connectors 3a and 3b. To allow this, in the light source device 1, the second thermal connector 3a and the first thermal connector 3b are formed of deformable materials, such as elastic members.

The second thermal connector 3a includes two first sensing electrodes 52a. The first sensing electrodes 52a are each provided in a position retreated from the connection surface of the second thermal connector 3a. The first thermal connector 3b includes two second sensing electrodes 52b. Like the first sensing electrodes 52a, the second sensing electrodes 52b are each provided in a position retreated from the connection surface of the first thermal connector 3b. The two second sensing electrodes 52b are connected to each other. Each of the first sensing electrodes 52a is connected to a conduction detector 53.

In the light source device 1, when the light source module 7 is provided in the slot 8, the pressure mechanism 38 applies force to the light source module 7 in a direction perpendicular to the surface of contact between the second thermal connector 3a and the first thermal connector 3b. As a result, the pressure mechanism 38 ensures electrical contact between the first sensing electrodes 52a and the second sensing electrodes 52b.

In other words, when the pressure mechanism 38 presses the light source module 7, the second thermal connector 3a and first thermal connector 3b, which are elastic members, are elastically deformed, and a reliable thermal connection is performed. In connection with this, the first sensing electrodes 52a and the second sensing electrodes 52b are brought into contact with each other and these electrodes are brought into electrical conduction.

The conduction detector 53 causes one of the first sensing electrodes 52a to flow current and detects that current flows from the other first sensing electrode 52a. Thus, the conduction detector 53 detects electrical conduction between the first sensing electrodes 52a and the second sensing electrodes 52b. Therefore, the control circuit 200 is able to detect a thermal connection between the first thermal connector 3b and the second thermal connector 3a.

According to the second modification described above, it is possible to confirm electrical conduction between the first sensing electrodes 52a and the second sensing electrodes 52b. Thus, the control circuit 200 is able to confirm a thermal connection between the second thermal connector 3a and the first thermal connector 3b.

[Third Modification to First Embodiment]

Next, a third modification to the above first embodiment will be described with reference to FIG. 7. For the sake of brevity, the figure shows only a portion of one slot 8. In this modification, the same structural elements as those of the above first embodiment are denoted by the same symbols as those of the first embodiment and their detailed descriptions are omitted.

Figure 7:
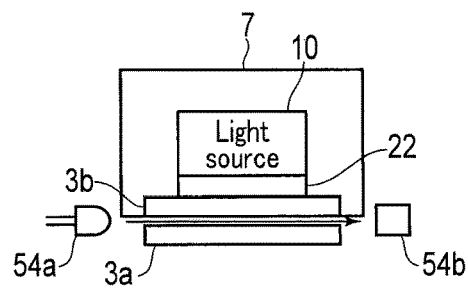
FIG. 7 is a schematic diagram showing a configuration for detecting a thermal connection of a third modification to the embodiment.

FIG. 7 is a schematic configuration diagram of a light source device for detecting a thermal connection according to the third modification to the first embodiment. The light source device 1 differs from that of the first embodiment in part of the structure of a connection between the light source module 7 and the slot 8 in the housing 2.

The light source device 1 according to the third modification detects a gap between the second thermal connector 3a and the first thermal connector 3b to detect a thermal connection between the first thermal connector 3b and the second thermal connector 3a. In other words, the light source device 1 includes a detecting light source (thermal connection detecting light source) 54a and a photodetector (PD) 54b corresponding to each slot 8 in the case 2. The thermal connection detecting light source 54a includes, for example, a light-emitting diode (LED). The photodetector 54b includes a photodiode (PD).

The thermal connection detecting light source 54a and the photodetector 54b are arranged opposite to each other such that they can transmit and receive light on the connection surface of the second thermal connector 3a.

The relationship in position between the thermal connection detecting light source 54a and the photodetector 54b is as follows. When the first thermal connector 3b and the second thermal connector 3a are separated from each other, the photodetector 54b detects light emitted from the thermal connection detecting light source 54a, and when the first thermal connector 3b and the second thermal connector 3a are connected to each other, the photodetector 54b does not detect light emitted from the thermal connection detecting light source 54a.

In the third modification, when each illumination module 7 is inserted in the slot 8, if there is a gap between the second thermal connector 3a and the first thermal connector 3b, the photodetector 54b detects light emitted from the thermal connection detecting light source 54a.

If there is no gap between the second thermal connector 3a and the first thermal connector 3b, the photodetector 54b does not detect light emitted from the thermal connection detecting light source 54a.

Therefore, the third modification makes it possible to detect a thermal connection between the first thermal connector 3b and the second thermal connector 3a according to whether the photodetector 54b detects light emitted from the thermal connection detecting light source 54a.

[Fourth Modification to First Embodiment]

Next, a fourth modification to the first embodiment will be described with reference to FIG. 8. In this modification, the same structural elements as those of the above first embodiment are denoted by the same symbols as those of the first embodiment and their detailed descriptions are omitted.

Figure 8:
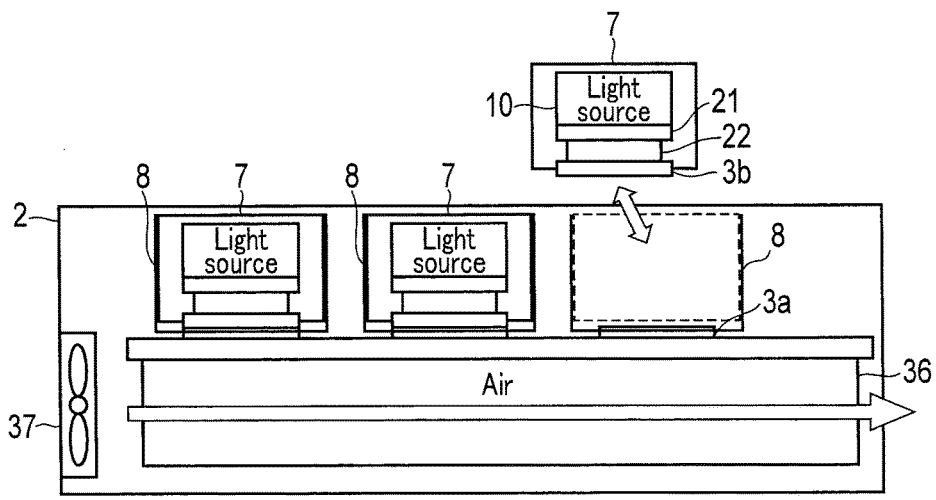
FIG. 8 is a schematic diagram showing a configuration of a heat exchange member of a fourth modification to the embodiment.

FIG. 8 is a schematic configuration diagram of a light source device for detecting a thermal connection according to the forth modification to the first embodiment. The light source device 1 partly differs from that of the first embodiment in the structure of a radiating member.

The light source device 1 of the fourth modification did not includes the heat pipe 35, but the heat sink 36 of the heat exchange member 5 is bonded to the underside of the second thermal connector 3a. The heat sink 36 is so laced that its fins extend in the longitudinal direction of the light source device 1. The air-sending fan 37 is placed to send air in a direction in which the fins formed in the heat sink 36 extend.

In this fourth modification, the heat generated from the light source 10 is conducted to the second thermal connector 3a through the heat conduction member 21, the temperature adjustment member 22 and the first thermal connector 3b. The heat conducted to the second thermal connector 3a is discharged from the heat sink 36 to the outside by air sent from the air-sending fan 37.

According to the fourth modification, therefore, the heat sink 36 is directly bonded to the second thermal connector 3a. As a result, the heat pipe 35 need not be provided. It is thus possible to reduce the number of members required for heat radiation.

Second Embodiment

Figure 9B:
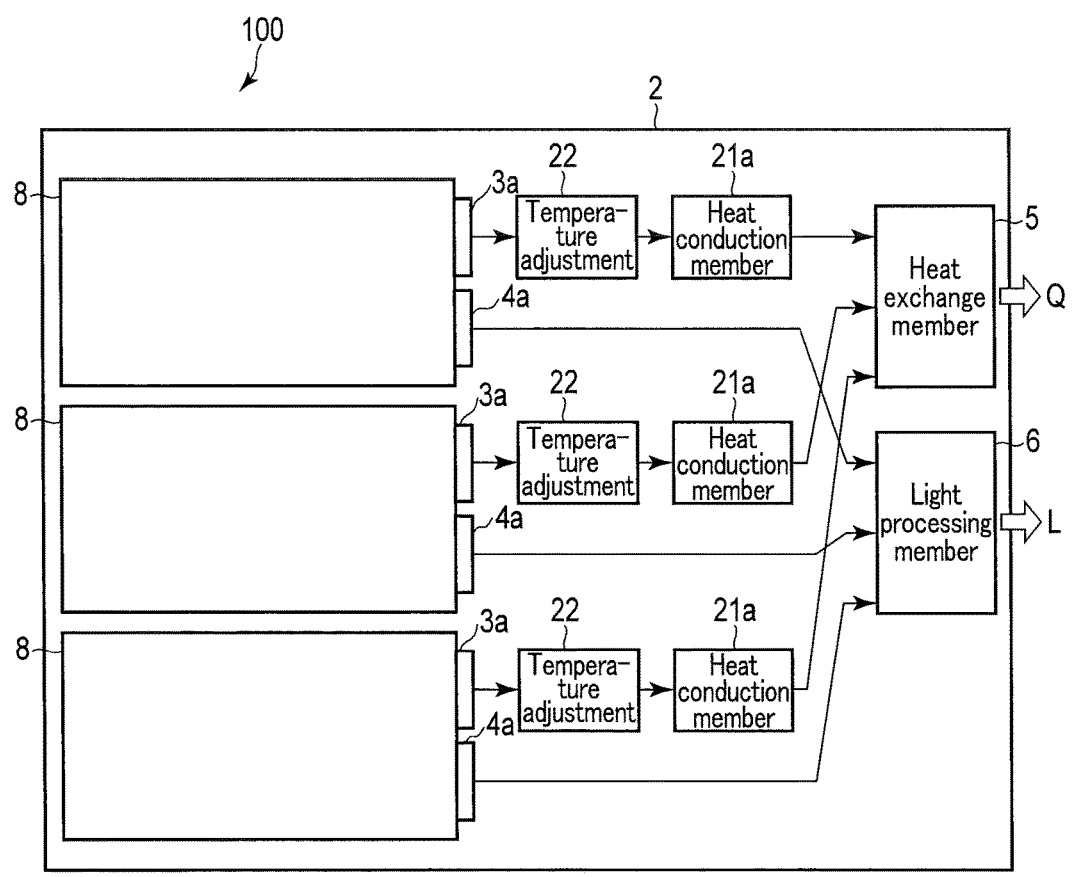
FIG. 9B is a block diagram showing a heat processing device for light source of the embodiment.

Next, a second embodiment of the present invention will be described below with reference to FIGS. 9A to 10. In this embodiment, the same structural elements as those of the above first embodiment are denoted by the same symbols as those of the first embodiment and their detailed descriptions are omitted.

FIG. 8 is a schematic configuration diagram of a light source device of the second embodiment. The light source device 1 differs from that of the first embodiment in placement of part of a member that conducts heat.

In this embodiment, the temperature adjustment member 22 placed in each light source module 7 is placed in the housing 2 in order to downsize the light source module 7. As shown in FIGS. 9A to 10, in the light source device 1, each light source module 7 includes the light source 10, a heat conduction member 21b, the first thermal connector 3b and the first optical connector 4b.

The light source module 7 can be attached to and detached from the corresponding slot 8. In the housing 2, a plurality of temperature adjustment members 22 and a plurality of heat conduction members 21a are placed. The number of temperature adjustment members 22 and the number of heat conduction members 21a each correspond to the number of light source modules 7 that can be placed, or the number of slots 8.

Each of the temperature adjustment members 22 is thermally connected to the second thermal connector 3a, which is provided at the slot 8 in which the temperature adjustment member 22 is provided, and to the heat conduction member 21a. For example, the second thermal connector 3a is placed on the top surface of the temperature adjustment member 22. The heat conduction member 21a is placed on the underside of the temperature adjustment member 22. The heat conduction members 21a are thermally connected to the heat exchange member 5 through heat pipes 35. Specifically, the heat conduction member 21a conducts heat from the temperature adjustment member 22 to the heat pipes 35. The heat pipes 35 are placed to penetrate the heat conduction members 21a.

As described above, in the second embodiment, the first heat processing unit 11 includes the heat conduction member 21b and the second heat processing unit includes the temperature adjustment member 22, the heat conduction member 21a and the heat exchange member 5. When the light source module 7 is attached to the slot 8, the second thermal connector 3a and the first thermal connector 3b are connected to each other on the flat underside of the slot 8, as shown in FIG. 10. However, the second optical connector 4a and the first optical connector 4b are optically connected to each other on a surface other than those of the first and second thermal connectors 3a and 3b, such as a side perpendicular to the underside of the slot 8. In other words, the second optical connector 4a is fixed to the side of the slot 8. In this case, the first optical connector 4b connected to the light source 10 of the light source module 7 through the optical fiber 31, is not fixed to the side of the light source module 7. Thus, the first optical connector 4b can freely be moved to a desired position.

Therefore, when a user attaches the light source module 7 to its corresponding slot 8, he or she first moves the first optical connector 4b to the position of the second optical connector 4a fixed to the side of the slot 8 and connects the first optical connector 4b to the second optical connector 4a. After that, the user holds the light source module 7 into the slot 8. It is desirable that the first and second optical connectors 4b and 4a have a structure of a common optical fiber connector, such as an FC connector and an MC connector.

In case that the light source module 7 is attached to the slot 8, the second optical connector 4a can be fixed in the housing 2, the optical fiber 31 having the first optical connector 4b at its end can be got out of the light source module 7, and the first optical connector 4b of the end of the optical fiber 31 can be connected to the second optical connector 4a. In this case, the slot 8 is provided with an opening for getting out the optical fiber 31 having the first optical connector 4b at its end. The first optical connector 4b can be fixed in the housing of the light source module 7 and the second optical connector 4a can be moved.

Next, an operation of the second embodiment will be described.

The light source device 1 is activated to emit light from the light source 10. Then, the light source 10 generates heat. The heat generated from the light source 10 is conducted to the heat conduction member 21b. The heat conducted to the heat conduction member 21b is conducted to the first thermal connector 3b. The heat conducted to the first thermal connector 3b is conducted to the temperature adjustment member 22 through the second thermal connector 3a.

If the temperature adjustment member 22 is a Peltier device, the temperature adjustment member 22 adjusts the temperature of the heat conduction member 21b through the thermal connectors 3a and 3b. Accordingly, the temperature adjustment member 22 is able to adjust the temperature of the light source 10 through the heat conduction member 21b. The heat conducted to the temperature adjustment member 22 is conducted to the heat conduction member 21a. The heat conducted to the heat conduction member 21a is conducted to the heat sink 36 that is a heat exchange member 5, through the heat pipes 35. The heat conducted to the heat pipes 35 is transmitted from high temperature to low temperature. In other words, the heat is conducted from the heat conduction member 21a toward the direction of the heat sink 36. The heat conducted to the heat sink 36 is radiated outside the housing 2 by air sent from the air-sending fan 37.

According to this embodiment, the temperature adjustment member 22 is placed in the housing 2 and thus the light source module 7 can be downsized more than that of the first embodiment.

The heat processing device for light source 100 according to this embodiment includes a plurality of temperature adjustment members 22, but the number of temperature adjustment members 22 may also be one. In other words, the light source device 1 can be so configured that heat generated from a plurality of light source modules 7 is transmitted to one temperature adjustment member 22. Like the number of temperature adjustment members 22, the number of heat conduction members 21a may also be one.

In the light source device 1 of this embodiment, the temperature adjustment members 22 are provided only in the housing 2 of the heat processing device for light source 100, but they can be provided in the light source module 7, too. In other words, the light source device 1 can be so configured that the temperature adjustment members 22 are provided in both the housing 2 and the light source module 7.

[Modification to Second Embodiment]

Next, a modification to the second embodiment will be described with reference to FIGS. 11A to 11C. The same structural elements as those of the above second embodiment are denoted by the same symbols as those of the second embodiment and their detailed descriptions are omitted.

The configuration of the light source device 1 of the modification to the second embodiment is almost the same as that of the light source device 1 of the second embodiment, but it differs in the configurations of the light source module 7 and the pressure mechanism 38.

In the light source device 1 of the modification, the light source module 7 is reliably inserted in the slot 8 by the pressure mechanism 38. In the modification, the first optical connector 4b is fixed to that side of the housing 2 which differs from the surface (underside) on which the thermal connector 3b of the light source module 7 is placed. Thus, the first and second optical connectors 4b and 4a are located to correspond to each other when the light source module 7 is inserted in the slot 8.

In the pressure mechanism 38 of the modification, a pressure member 41a is provided in the cover fixing member 41. The pressure member 41a is a rod or a plate extending in a perpendicularly downward direction from the cover fixing member 41. When the cover fixing member 41 is not present on the cover section 43 of the slot 8, the pressure member 41a is held in space formed on the side of the slot 8. When the cover fixing member 41 slides on the cover section 43, the pressure member 41a moves into the slot 8 from the space. Then, the pressure member 41a is brought into contact with a side opposed to the side on which the first optical connector 4b of the light source module 7 is placed, and presses the light source module 7 toward the direction of the second optical connector 4a.

Next, an operation of this modification will be described.

As shown in FIG. 11A, the light source module 7 is inserted in the slot 8. At this time, the thermal connector 3a and the first thermal connector 3b are not reliably connected to each other. The second thermal connector 4a and the first thermal connector 4b are displaced from each other in the vertical direction and are not optically connected to each other.

After that, as shown in FIG. 11B, when the cover section 43 is closed, it presses the light source module 7. Accordingly, the second thermal connector 3a and the first thermal connector 3b are brought into contact with each other and thermally connected to each other. The second optical connector 4a and the first optical connector 4b are arranged opposite to each other. However, the second optical connector 4a and the first optical connector 4b are not connected to each other.

Furthermore, as shown in FIG. 11C, when the cover fixing member 41 is slid onto the cover section 43, the cover section 43 is prevented from opening accidentally. Thus, the second thermal connector 3a and the first thermal connector 3b are reliably connected to each other. In this case, as the cover fixing member 41 slides, the pressure member 41a also slides in the horizontal direction and thus the light source module 7 is pressed toward the direction of the second optical connector 4a by the pressure member 41a. Accordingly, the first optical connector 4b provided in the light source module 7 and the second optical connector 4a provided on the side of the slot 8 are optically connected to each other.

According to this modification, the thermal connectors 3a and 3b and the optical connectors 4a and 4b are connected at different timings by the pressure mechanism 38. Specifically, the second thermal connector 3a and the first thermal connector 3b are provided to connect the light source module 7 and the second heat processing unit (heat pipe 35, heat sink 36 and air-sending fan 37) thermally in a first connecting direction. The optical connectors 4a and 4b are provided to connect the light source module 7 and the light processing member 5 optically in a second connecting direction.

The timing at which the light source module 7 and the second heat processing unit (heat pipe 35, heat sink 36 and air-sending fan 37) are connected thermally in the first connecting direction and the timing at which the light source module 7 and the light processing member 5 are connected optically in the second connecting direction when the light source module 7 is attached to the housing 2, are slightly different from those in the second embodiment described above.

As a result, the second and first thermal connectors 3a and 3b and the second and first optical connectors 4a and 4b are connected step by step. The light source module 7 is reliably inserted in the slot 8. In other words, the second thermal connector 3a and the first thermal connector 3b are thermally connected with reliability. Substantially at the same time, the second optical connector 4a and the first optical connector 4b are optically connected with reliability.

It is one example that is given in this modification. If the same connection as described above is achieved, another configuration can be adopted.

The foregoing embodiments are not limited to the above descriptions but the respective embodiments can be combined. For example, the pressure mechanism 38 of the modification to the second embodiment can be applied to the light source device 1 of the first embodiment.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A light source device comprising:
a housing;
a plurality of light source units which are attachable to and detachable from the housing and which output light;
a plurality of first heat processing units which are respectively provided in the plurality of light source units and which process heat generated from the plurality of light source units;
a second heat processing unit which is provided in the housing and which processes heat conducted from each of the plurality of first heat processing units;
a plurality of thermal connectors which make the plurality of first heat processing units and the second heat processing unit attachable to and detachable from each other and which thermally connect the plurality of first heat processing units and the second heat processing unit;

a light processing unit which is provided in the housing and which processes the light output from the plurality of light source units; and a plurality of optical connectors which make the plurality of light source units and the light processing unit attachable to and detachable from each other and which optically connect the plurality of light source units and the light processing unit, wherein the housing comprises a plurality of slots to which the plurality of light source units are configured to respectively attach in an attached configuration, wherein one of the plurality of thermal connectors is on a surface of one of the plurality of slots, and in the attached configuration, the plurality of first heat processing units and the second heat processing unit are thermally connected to each other by way of each of the plurality of thermal connectors, wherein the second heat processing unit comprises one or more second heat processing units and a number of the one or more second heat processing units is less than the number of the plurality of light source units.

2. The light source device of claim 1, wherein
the second heat processing unit includes a heat exchange unit to which the heat generated from the plurality of light source units is conducted and which radiates the heat outside the housing.

3. The light source device of claim 1, wherein
the plurality of first heat processing units each include temperature adjustment unit which adjusts temperature of the light source unit.

4. The light source device of claim 1, wherein
the second heat processing unit includes at least one temperature adjustment unit which adjusts temperatures of the plurality of light sources through the plurality of thermal connectors.

5. The light source device of claim 1, wherein
the plurality of thermal connectors each include a thermal connection detection unit which detects that the first heat processing unit and the second heat processing unit are thermally connected.

6. The light source device of claim 2, wherein
the second heat processing unit includes a high temperature conduction unit which thermally connects the plurality of thermal connectors and the heat exchange unit.

7. The light source device of claim 1, wherein
the plurality of thermal connectors thermally connect the plurality of first heat processing units and the second heat processing unit in a first connecting direction;
the plurality of optical connectors optically connect the plurality of light source units and the light processing unit in a second connecting direction; and
when the plurality of light source units are each attached to the housing, timing of thermal connection in the first connecting direction and timing of optical connection in the second connecting direction are different.

8. The light source device of claim 1, wherein
the plurality of optical connectors each include a first optical connector and a second optical connector which are connectable to and separated from each other;
the first optical connector is connected to the light source unit through an optical fiber;
the second optical connector is connected to the light processing unit through an optical fiber; and
one of the first optical connector and the second optical connector is movable.

9. The light source device of claim 1, further comprising:
a pressure mechanism which applies pressing force to the plurality of thermal connectors when the plurality of light source units are each attached to the housing.

10. The light source device of claim 1, wherein
when one of the plurality of light source units is attached to the housing, the optical connector optically connects the light source unit and the light processing unit to allow the light output from the light source unit to be propagated to the light processing unit.

11. The light source device of claim 1, further comprising:
a plurality of electrical connectors which connect electrical wiring to each of the plurality of light source units;
wherein
when one of the plurality of light source units is attached to the housing, the electrical connector connects the electrical wiring to the light source unit to apply power necessary for operation to the light source unit.

12. The light source device of claim 5, wherein
the plurality of thermal connectors each include a first thermal connector and a second thermal connector which are connectable to and separated from each other;
the first thermal connector is provided in the first heat processing unit;
the second thermal connector is provided in the second heat processing unit; and
the thermal connection detection unit includes:
    a first sensing electrode provided in the first thermal connector;
    a second sensing electrode provided in the second thermal connector; and
    a detector which detects that the first thermal connector and the second thermal connector are thermally connected, by detecting conduction states of the first sensing electrode and the second sensing electrode.

13. The light source device of claim 5, wherein
the plurality of thermal connectors each include a first thermal connector and a second thermal connector which are connectable to and separated from each other;
the first thermal connector is provided in the first heat processing unit;
the second thermal connector is provided in the second heat processing unit;
the thermal connection detection unit includes a thermal connection detecting light source which emits light and a photodetector which detects the light emitted from the thermal connection detecting light source; and
a relationship in position between the thermal connection detecting light source and the photodetector is that when the first thermal connector and the second thermal connector are separated, the photodetector detects the light emitted from the thermal connection detecting light source and when the first thermal connector and the second thermal connector are connected, the photodetector does not detect the light emitted from the thermal connection detecting light source.

14. The light source device of claim 1, wherein
the plurality of light source units include a laser diode.

15. A light source device comprising:
a housing;
a plurality of light source units which are attachable to and detachable from the housing and which output light;

a plurality of first heat processing units which are respectively provided in the plurality of light source units and which process heat generated from the plurality of light source units;
a second heat processing unit which is provided in the housing and which processes heat conducted from each of the plurality of first heat processing units;
a plurality of thermal connectors which make the plurality of first heat processing units and the second heat processing unit attachable to and detachable from each other and which thermally connect the plurality of first heat processing units and the second heat processing unit;
a light processing unit which is provided in the housing and which processes the light output from the plurality of light source units; and
a plurality of optical connectors which make the plurality of light source units and the light processing unit attachable to and detachable from each other and which optically connect the plurality of light source units and the light processing unit,
wherein the housing comprises a plurality of slots to which the plurality of light source units are configured to respectively attach in an attached configuration,
wherein one of the plurality of thermal connectors is on a surface of one of the plurality of slots, and
in the attached configuration, the plurality of first heat processing units and the second heat processing unit are thermally connected to each other by way of each of the plurality of thermal connectors, wherein the plurality of thermal connectors each include a thermal connection detection unit which detects that the first heat processing unit and the second heat processing unit are thermally connected, and
wherein the plurality of thermal connectors each include a first thermal connector and a second thermal connector which are connectable to and separated from each other;
the first thermal connector is provided in the first heat processing unit and includes a portion of low-heat resistance;
the second thermal connector is provided in the second heat processing unit and includes a portion of low-heat resistance; and
the thermal connection detection unit includes:
 a first temperature sensor placed in the portion of low-heat resistance of the first thermal connector;
 a second temperature sensor placed in the portion of low-heat resistance of the second thermal connector; and
 a detector which detects that the first thermal connector and the second thermal connector are thermally connected, based upon a temperature difference between temperature sensed by the first temperature sensor and temperature sensed by the second temperature sensor.

16. A light source device comprising:
a housing;
a plurality of light source units which are attachable to and detachable from the housing and which output light;
a plurality of first heat processing units which are respectively provided in the plurality of light source units and which process heat generated from the plurality of light source units;
a second heat processing unit which is provided in the housing and which processes heat conducted from each of the plurality of first heat processing units;
a plurality of thermal connectors which make the plurality of first heat processing units and the second heat processing unit attachable to and detachable from each other and which thermally connect the plurality of first heat processing units and the second heat processing unit;
a light processing unit which is provided in the housing and which processes the light output from the plurality of light source units; and
a plurality of optical connectors which make the plurality of light source units and the light processing unit attachable to and detachable from each other and which optically connect the plurality of light source units and the light processing unit,
wherein the housing comprises a plurality of slots to which the plurality of light source units are configured to respectively attach in an attached configuration,
wherein one of the plurality of thermal connectors is on a surface of one of the plurality of slots, and
in the attached configuration, the plurality of first heat processing units and the second heat processing unit are thermally connected to each other by way of each of the plurality of thermal connectors, wherein the plurality of thermal connectors each include a thermal connection detection unit which detects that the first heat processing unit and the second heat processing unit are thermally connected, and
wherein the plurality of thermal connectors each include a first thermal connector and a second thermal connector which are connectable to and separated from each other;
the first thermal connector is provided in the first heat processing unit and includes a portion of low-heat resistance;
the second thermal connector is provided in the second heat processing unit and includes a portion of low-heat resistance; and
the thermal connection detection unit includes:
a first sensor placed in the portion of low-heat resistance of the first thermal connector;
a second sensor placed in the portion of low-heat resistance of the second thermal connector; and
a detector which detects that the first thermal connector and the second thermal connector are thermally connected, based upon sensing results of the first and second sensors.

\* \* \* \* \*